US011994839B2

(12) United States Patent
Ueda et al.

(10) Patent No.: US 11,994,839 B2
(45) Date of Patent: May 28, 2024

(54) OPTIMIZATION SYSTEM OF MANUFACTURING PROCESS AND METHOD THEREOF

(71) Applicant: Hitachi, Ltd., Tokyo (JP)

(72) Inventors: Atsuko Ueda, Tokyo (JP); Shigenori Matsumoto, Tokyo (JP)

(73) Assignee: HITACHI, LTD., Tokyo (JP)

( * ) Notice: Subject to any disclaimer, the term of this patent is extended or adjusted under 35 U.S.C. 154(b) by 0 days.

(21) Appl. No.: 17/775,397

(22) PCT Filed: Oct. 15, 2020

(86) PCT No.: PCT/JP2020/038856
§ 371 (c)(1),
(2) Date: May 9, 2022

(87) PCT Pub. No.: WO2021/095428
PCT Pub. Date: May 20, 2021

(65) Prior Publication Data
US 2022/0390923 A1 Dec. 8, 2022

(30) Foreign Application Priority Data
Nov. 15, 2019 (JP) ................................ 2019-206793

(51) Int. Cl.
G05B 19/4155 (2006.01)
(52) U.S. Cl.
CPC ............. G05B 19/4155 (2013.01); *G05B 2219/31449* (2013.01)
(58) Field of Classification Search
CPC ............ G05B 19/4155; G05B 2219/31449
(Continued)

(56) References Cited

U.S. PATENT DOCUMENTS

2002/0143417 A1   10/2002  Ito et al.
2006/0231752 A1*  10/2006  Houge ................. G01N 23/203
                                              250/306
(Continued)

FOREIGN PATENT DOCUMENTS

JP    2002-287803 A   10/2002
JP    2003-345416 A   12/2003
(Continued)

OTHER PUBLICATIONS

International Search Report of PCT/JP2020/038856 dated Dec. 22, 2020.

*Primary Examiner* — Jigneshkumar C Patel
(74) *Attorney, Agent, or Firm* — MATTINGLY & MALUR, PC (57) ABSTRACT

A problem is to specify a more proper manufacturing process for a product as a material. A configuration of the present invention for solving the above problem is a manufacturing process optimization system 1 which includes an input device 12 which receives a final product and information on its manufacturing process, a central control device 11 which in accordance with a product management unit 21 stored in a main storage device 14, separates each process block constituting the manufacturing process into functions that the process thereof is responsible for, and selects the sensitivity of each separated function along the manufacturing process to thereby calculate process conditions in all manufacturing process, and an output device 13 which outputs the process conditions.

8 Claims, 9 Drawing Sheets

(58) Field of Classification Search
USPC .......................................................... 700/28
See application file for complete search history.

(56) References Cited

U.S. PATENT DOCUMENTS

| | | |
|---|---|---|
| 2006/0282186 A1 | 12/2006 | Hansen et al. |
| 2007/0067056 A1* | 3/2007 | Nishinohara .... G05B 19/41885 700/121 |
| 2011/0098862 A1 | 4/2011 | Andrei et al. |
| 2011/0288691 A1* | 11/2011 | Abe ...................... H01M 10/48 700/297 |
| 2016/0011589 A1* | 1/2016 | Yamada .................. H01L 22/20 700/110 |
| 2020/0110385 A1* | 4/2020 | Yu .................... G05B 19/41875 |

FOREIGN PATENT DOCUMENTS

| | | | |
|---|---|---|---|
| JP | 2006004428 A | * | 1/2006 |
| JP | 2006-326683 A | | 12/2006 |
| JP | 2013-508881 A | | 3/2013 |
| JP | 2016-081185 A | | 5/2016 |
| JP | 2019-021343 A | | 2/2019 |
| WO | 2019/012002 A1 | | 1/2019 |

* cited by examiner

| PRODUCT P1 | PROCESS CONDITION P-A1a | PROCESS CONDITION P-A1b | PROCESS CONDITION P-A2a | PROCESS CONDITION P-B1a | PROCESS CONDITION P-B2a | PROCESS CONDITION P-B2b | PROCESS CONDITION P-C1a |
|---|---|---|---|---|---|---|---|
| FUNCTION A1 | ○ | ○ | | | | | ○ |
| FUNCTION A2 | | | ○ | | ○ | | |
| FUNCTION B1 | ○ | | | | | | |
| FUNCTION B2 | | | ○ | | | | ○ |
| FUNCTION B3 | | ○ | | | ○ | | ○ |
| FUNCTION C1 | | | | ○ | | ○ | |

FIG. 15

| PRODUCT P1 | MATERIAL ATTRIBUTE M-A1a | MATERIAL ATTRIBUTE M-A1b | MATERIAL ATTRIBUTE M-A2a | MATERIAL ATTRIBUTE M-B1a | MATERIAL ATTRIBUTE M-B1b | MATERIAL ATTRIBUTE M-C1a | MATERIAL ATTRIBUTE M-C1b |
|---|---|---|---|---|---|---|---|
| FUNCTION A1 | ○ | | | ○ | ○ | | |
| FUNCTION A2 | | | ○ | ○ | | | |
| FUNCTION B1 | | ○ | | | | | ○ |
| FUNCTION B2 | ○ | | | ○ | | | |
| FUNCTION B3 | | | | | ○ | ○ | |
| FUNCTION C1 | | | ○ | | | | ○ |

OPTIMIZATION SYSTEM OF MANUFACTURING PROCESS AND METHOD THEREOF

TECHNICAL FIELD

The present invention relates to a technique of optimizing a manufacturing process comprised of a plurality of configurations.

BACKGROUND ART

Conventionally, optimization of a process in the manufacture of a material is performed not only on a material as a base material but also on a product such as a machine or the like. Quality control of the product is performed by defining for each element constituting the product, its role and behavior as functions and managing the quality expressed by the connection of the functions inclusive of the conditions of a manufacturing process. On the other hand, the material changes its mode from the starting material to the finally-obtained product.

Therefore, in the control of the quality of manufactured materials, in order to quickly find out the manufacturing process and process conditions that become the cause for improvement against defects in the final product, the mode of an intermediate material produced in an intermediate process is deeply involved. Depending on the conditions in each manufacturing process, the material properties of the product obtained in the middle process of manufacturing are greatly affected, and this also affects the properties of the finally-obtained product. In these days when responsibility for material manufacturing is required, information on an intermediate production process is also required to ensure quality, and the manufacturing of environment-friendly products is required in consideration of the environmental impact of intermediate products.

Generally, the conditions in each manufacturing process, the material properties finally obtained, and the like have been held in a database.

When an unexpected defect occurs in the use of a material, it may be necessary to go back to the upstream manufacturing process in order to quickly investigate the cause and review the manufacturing process. Further, even when it becomes necessary to change the material properties due to changes in product specifications, it is necessary to review the manufacturing process in like manner. However, finding the cause in the upstream process using the above-mentioned database usually requires a lot of labor and costs.

Patent Literature 1 is a method for optimizing a manufacturing process for manufacturing a casting or a molded product manufactured by one or more manufacturing steps with respect to preset parameters.

CITATION LIST

Patent Literature

PTL 1: Japanese Patent Application Laid-Open No. 2006-326683

SUMMARY OF INVENTION

Technical Problem

The system of Patent Literature 1 is a method or system of optimizing the manufacturing process of a casting or a molded product produced by one or more manufacturing steps with respect to parameters preset for optimal values by simulation using a computer.

Patent Literature 1 does not refer to the correspondence relation between the characteristics and the factors, such as the material properties like manufacturing blocks arising from which of process conditions like manufacturing process blocks.

Therefore, an object of the present invention is to manage an intermediate production process for a product as a material and to optimize a manufacturing process that quickly responds to changes in manufacturing requirements, etc.

Solution to Problem

In order to achieve the above object, in the present invention, a functional sensitivity in a control factor corresponding to a characteristic affecting target physical properties and the like is specified, and the functional sensitivity is adjusted to optimize a process. The control factor indicates a control factor in manufacturing, and includes, for example, a material attribute indicating the attribute of each material/intermediate product, and a process condition thereof.

A more detailed configuration of the present invention is an optimization system of a manufacturing process comprised of a plurality of processes, which includes an input device which receives factor information including a control factor in each of the processes, and restriction information serving as a restriction in the manufacturing process, a main storage device which stores a program therein, a central control device which in accordance with the program, calculates a functional sensitivity indicative of the degree of an influence to the manufacturing process by using the factor information and functions exhibitable by each product produced in the manufacturing process, selects the control factor on the basis of the functional sensitivity, specifies a physical property of an intermediate product in each process by using the selected control factor, and determines using the specified physical property of each intermediate product whether the control factor satisfies a predetermined condition, and an output device which outputs the control factor having satisfied the predetermined condition. Further, the present invention also includes a method using this system and a program product for executing the method.

Advantageous Effects of Invention

According to the present invention, it is possible to specify a more appropriate manufacturing process.

DESCRIPTION OF EMBODIMENTS

Hereinafter, a mode (called "the present embodiment") for carrying out the present invention will be described in detail with reference to the drawings and the like. The present embodiment is an example of a chemical plant which manufactures one or a plurality of final products from one or a plurality of raw materials.

Terms and the Like

A process is each individual processing process in the manufacture of materials. The process has a context with other processes. An example of the process includes compounding, coating, heating, cooling, stirring, distillation, or the like. A plurality of processes configure a manufacturing process of producing final products.

A raw material is a substance accepted by the chemical plant. An example of the raw material includes a resin, crude oil, iron ore, coal, limestone, or the like.

The intermediate product is a substance which temporarily exists between one process and another process. An example of the intermediate product includes benzene, naphtha, a mixture of them, or the like.

The final product is a substance produced by the chemical plant as a product. An example of the product includes fuels, paints, chemicals, chemical fibers, resins, or the like. Other industrial products (aircraft parts, clothing, containers, hygiene products, artificial organs, etc.) are manufactured from the chemical fibers, resins or the like.

The function is a function according to the use of the product. An example of the function includes a drying speed, an oxidation rate (easiness to rust), disinfection ability, detergency, heat insulation ability, heat resistance, sound-proofing ability, tensile strength, viscosity, adhesive force, ignition speed, malleability, ductility, or the like. The function according to the usage of the final product is directly linked to the market evaluation of the final product.

(Manufacturing Process Optimization System)

Figure 1:
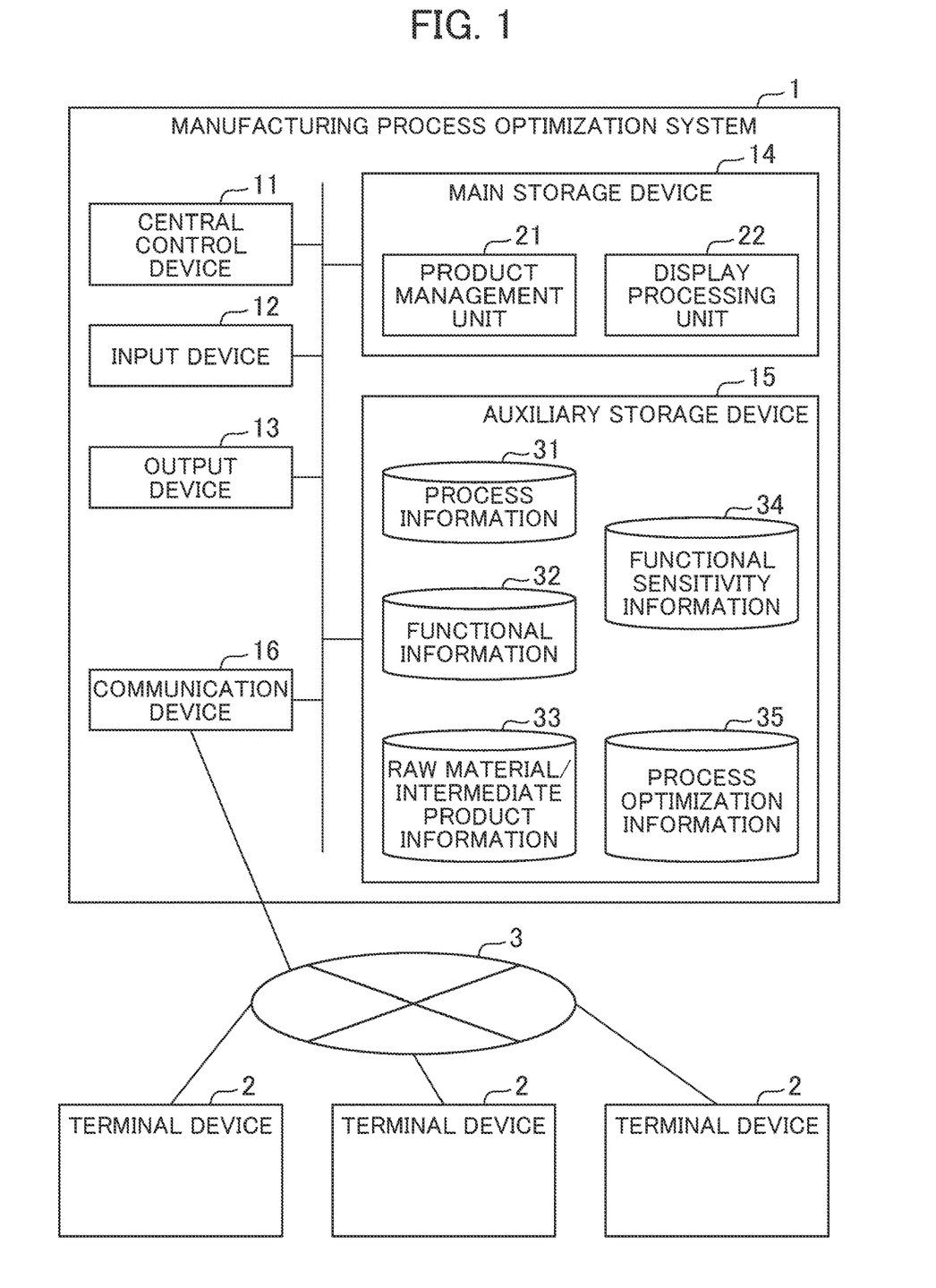
FIG. 1 is a diagram describing a configuration of a manufacturing process optimization system.

FIG. 1 is a diagram describing a configuration of a manufacturing process optimization system 1. The manufacturing process optimization system 1 is a general computer and includes a central control device 1, an input device 12 such as a mouse and a keyboard, a display, a speaker, an output device 13 such as a printer or the like, a main storage device 14, and an auxiliary storage device 15 (storage unit).

These are connected to each other by a bus. The auxiliary storage device 15 stores therein process information 31, functional information 32, raw material/intermediate product information 33, functional sensitivity information 34, and process optimization information 35.

A product management unit 21 and a display processing unit 22 in the main storage device 14 are programs. The central control device 11 reads these programs from the auxiliary storage device 15 to load them into the main storage device 14, thereby realizing functions of the respective programs (details there will be described later). The auxiliary storage device 15 may be configured independently of the manufacturing process optimization system 1. Note that the "manufacturing process" in the present embodiment shows a procedure for producing a product, and the "optimization" means that a more appropriate control factor is obtained from a plurality of control factors including material attributes and process conditions.

Also, in the present embodiment, the manufacturing process optimization system 1 may be realized (made into server) with the so-called cloud. As shown in FIG. 1, the manufacturing process optimization system 1 is connected to terminal devices 2 installed at each manufacturing base and design base, or the like through a network 3 from a communication device 16. Further, with the operation of each terminal device 2, the manufacturing process optimization system 1 may be configured to perform operation. In this case, each terminal device 2 has an input device and an output device (screen). In addition, the input device 12 and the output device 13 of the manufacturing process optimization system 1 may be omitted.

(Processing Procedure)

Figure 2:
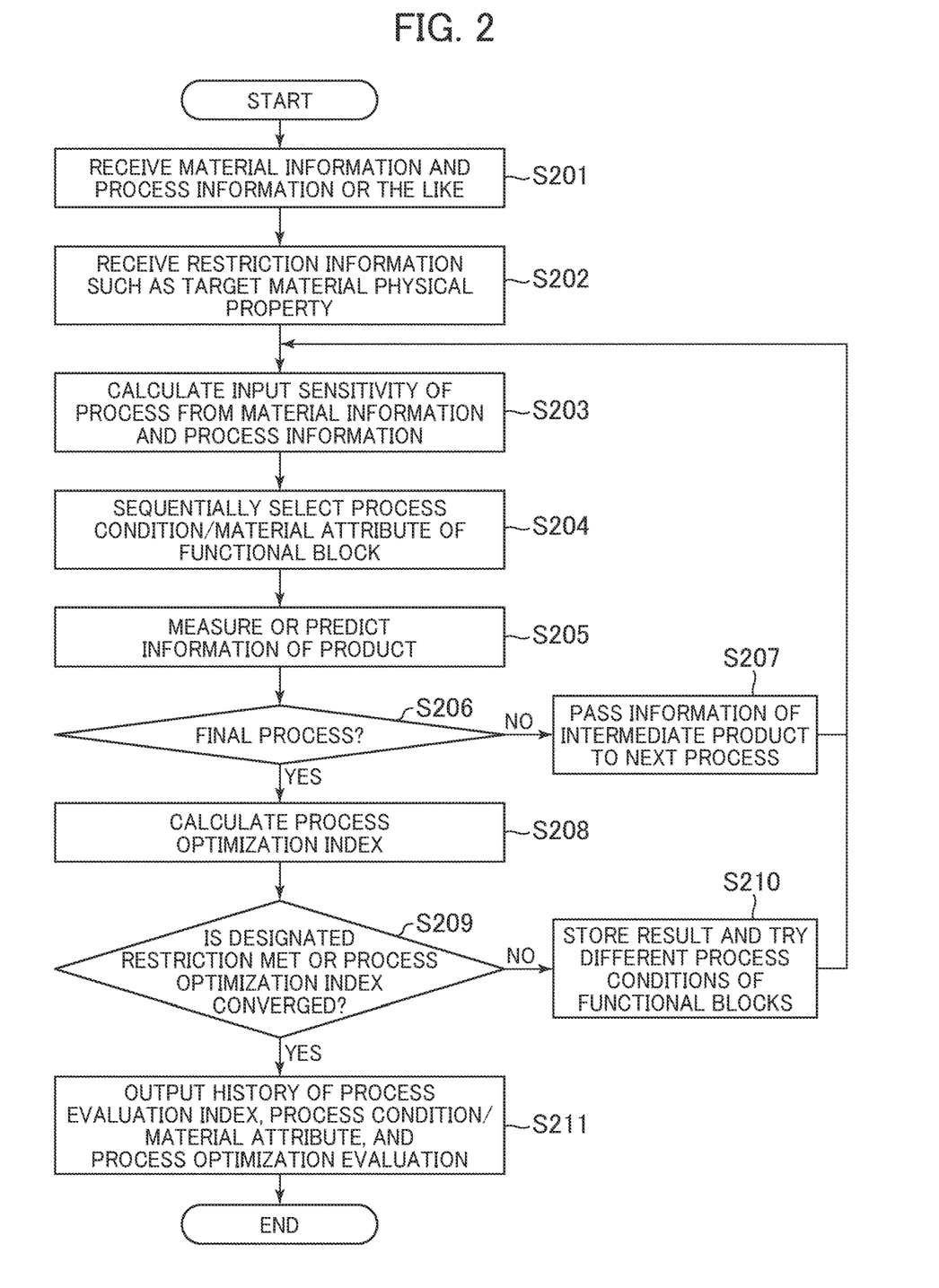
FIG. 2 is a flow chart of a processing procedure.

FIG. 2 is a flow chart of a processing procedure of the manufacturing process optimization system 1. The manufacturing process optimization system 1 is a system which calculates the sensitivity of a function by using material information input thereto and factor information such as the accepted process information 31, etc. and sequentially selects the functional sensitivity according to the flow of the process, thereby predicting an intermediate product or a final product.

In Step S201, according to the product management unit 21 of the manufacturing process optimization system 1, the central control device 11 receives the process information 31 input via the input device 12 from a user, the functional information 32 that the product exerts, process information including process conditions related to each process, and raw material information (hereinafter called material information) including material attributes regarding raw materials for manufacturing. Here, the process information and the material information may be accepted as factor information including control factors of a process consisting of at least one of them.

Incidentally, hereinafter, when the central control device 11 performs processing in accordance with the product management unit 21 and the display processing unit 22, it represents the product management unit 21 and the display processing unit 22 as the subject.

It is sufficient for the raw material information to simply recognize the type of material and the amount thereof. Specifically, the raw material information may be a CAS registry number, a molecular structure, a blending amount, a blending recipe, or a ratio.

In Step S202, the product management unit 21 receives restriction information concerning the manufacture input via the input device 12 from the user. A specific example of the restriction information includes target material properties, the yield of an intermediate product (or final product), a manufacturing time, or the like.

In Step S203, the product management unit 21 calculates the sensitivity of a function from the input material information and process information, and the functional information 32. The sensitivity is information indicating the degree of relevance (influence) to the manufacturing process for each control factor (process condition, material attribute, etc.) relative to the function of the product. Here, the material information and the process information may be replaced with the factor information.

Figure 12:
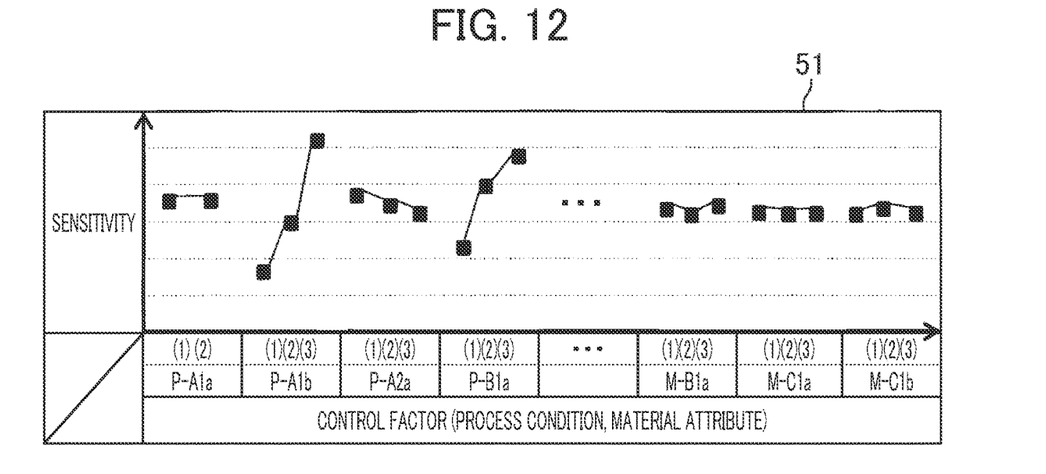
FIG. 12 is a diagram describing a factor effect diagram.

The calculated sensitivity of the function (hereinafter called functional sensitivity) is stored in the functional sensitivity information 34 together with the information indicative of relevance to the received material information. At this time, the functional sensitivity is displayed as a factor effect diagram on the output device 13 by the display processing unit 22. An example thereof is shown in FIG. 12. As shown in FIG. 12, as for each sensitivity, a plurality of values obtained by changing parameters ((1), (2), etc.) with respect to each control factor are calculated and displayed.

Incidentally, in the present Step, the display of the factor effect diagram may be omitted. Therefore, the details of the present diagram will be described later.

Next, in Step S204, the input device 12 or the product management unit 21 sequentially selects a process condition and a material attribute to be considered, according to the order of the process in regard to the functional sensitivity of the factor effect diagram (refer to FIG. 12) displayed in S203. Here, the term "sequentially" means accepting selection from the upstream side of the manufacturing process. Incidentally, this selection may be in the form of selecting the control factor.

Figure 14:
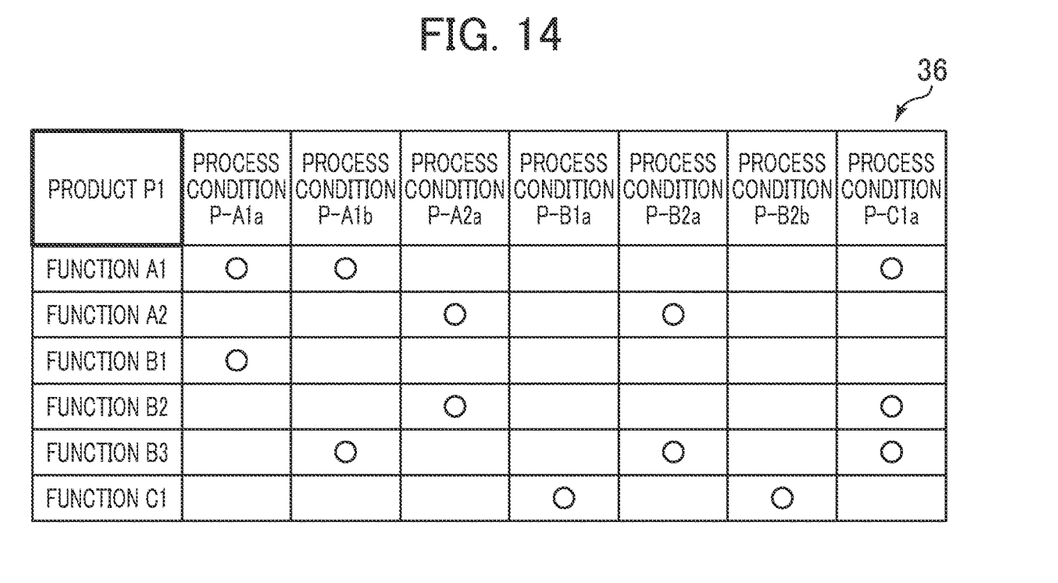
FIG. 14 is a diagram describing function/process related information.
Figure 15:
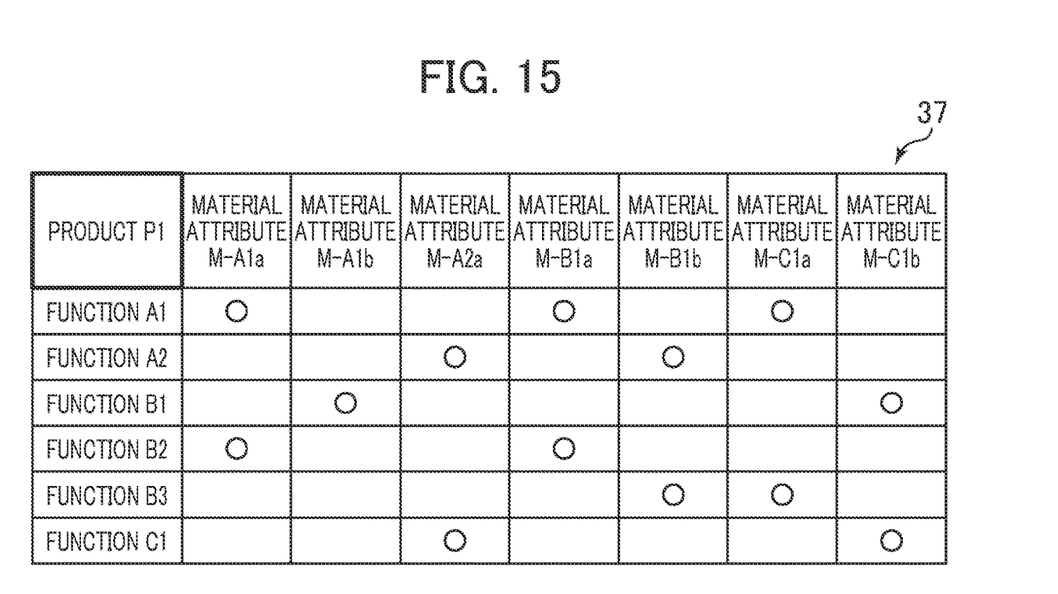
FIG. 15 is a diagram describing function/material related information.

Further, the selection is performed in accordance with function/process related information 36 and function/material related information 37 shown in FIGS. 14 and 15. That is, in FIGS. 14 and 15, a process condition and a material attribute each given with "o" are selected for each function included in the functional information received in Step S201. For example, when a function A1 is received in Step S201, process conditions P-A1a, P-A1b, and P-C1a, and material attributes M-A1a, M-B1a, and M-C1a are selected. Here, the function/process related information 36 and the function/material related information 37 may be collectively treated as function/factor related information.

Incidentally, instead of "0", "numbers" may be used in the function/process related information 36 shown in FIGS. 14 and 15. In this case, a number indicating the degree of sensitivity is stored in each area, and a process condition and a material attribute in which a number greater than or equal to a threshold value=sensitivity is recorded may be selected. Further, when using the numbers, the process condition and the material attribute for the number indicative of the maximum value may be selected out of the corresponding process conditions and material attributes. The details of the function/process related information 36 shown in FIGS. 14 and 15 will be described later.

Furthermore, information indicating the presence or absence such as "o" or information indicating symbols other than the numbers may be used. This corresponds to information indicating multiple types such as o,Δ,x. Then, a process condition and a material attribute for the selected symbols such as only o, or o and Δ, etc. are selected.

Then, the process condition and material attribute selected by the product management unit 21 are stored in the process optimization information 35 together with the input material information and process information.

Further, the present selection may be performed collectively in plural, or its order may be any order. However, in Step S206 to be described later, it is necessary to be able to confirm the completion of selection in each process.

Next, in Step S205, the product management unit 21 predicts an intermediate product from the combination of the control factor (process condition and material attribute) selected in Step S204 and the functional density corresponding to the same. This prediction uses the functional sensitivities for every parameter ((1), (2), etc.) calculated in Step S203 for the control factors selected in Step S204. Then, as for these functional sensitivities, the functional sensitivities at which the parameters are changed like the factor effect diagram shown in FIG. 12 are displayed for each control factor. That is, in the present Step, the information selected in Step S204 is selectively displayed from the factor effect diagram displayed in Step S202.

Then, in the displayed factor effect diagram, the functional sensitivity is selected for each control factor from the displayed functional sensitivities via the input device 12. The parameter corresponding to the selected functional sensitivity is specified and the prediction is executed using the same.

Here, the details of the factor effect diagram, and the details of selection using the same will be described using FIGS. 12 and 13.

The horizontal axis of the factor effect diagram shown in FIG. 12 indicates the process condition and the material attribute. The process condition and the material attribute are "control factors" each indicative of the value that can be controlled by the user of the system. The control factors in the present embodiment include the process condition and the material attribute. Further, P-A1a to M-C1b for the control factors respectively correspond to the process conditions and the material attributes shown in FIGS. 14 and 15. Incidentally, the upstream side to the downstream side are shown in the order of "A" to "C" each indicating the process.

Further, the numbers placed between parentheses for each control factor are for identifying the parameters of the control factors. Therefore, the sensitivities plotted on FIG. 12 are shown as the sensitivities where the parameters are changed for each control factor.

The vertical axis of the factor effect diagram 51 indicates the sensitivity of the process condition or the material attribute for each function. This is input in Step S203 as described above. The sensitivity of the function indicates the magnitude at which the function is developed for a certain process condition or material attribute. It may be the average slope of a signal-to-noise ratio (S/N ratio) or the squared value. The sensitivity may be calculated from the input material information.

The signal-to-noise ratio is a value by dividing the variance of a signal of a certain physical quantity by the variance of noise. The larger the signal-to-noise ratio, the smaller the effect of noise.

Further, (1), (2), etc. in the factor effect diagram of FIG. 12 show where the parameters of the control factors thereof are changed as described above. For example, the material attribute (M-) shows a change in the sensitivity when the raw material attribute is changed. Further, the process condition (P-) shows a change in the sensitivity when the conditions such as processing (heating temperature, processing time, pressure, etc.) are changed.

The factor effect diagram 51 is created for each product. Looking at FIG. 12, the following can be seen.

The sensitivities for the functions of P-A1b and P-B1a for the control factors vary widely and have a great effect on the functions. That is, it becomes possible to relatively affect the functions by changing the parameters.

It can be seen that the functional sensitivities for the control factors other than P-A1b and P-B1a for the control factors are about the same level and are not significantly affected. That is, even if the parameters are changed, the functions are not affected relatively.

Thus, when the above-described parameters of the control factors large in variation are changed, the functions of the subsequent intermediate product and final product are adjusted effectively. That is, it becomes possible to efficiently adjust the control of manufacture for the final product having the target characteristics. Therefore, the selection of the functional sensitivity in the present Step may be performed as follows in addition to doing it manually via the input device 12. The product management unit 21 may be configured to select a functional sensitivity change rate of a predetermined value or more (slope more than the predetermined one) where the parameters are changed.

Figure 13:
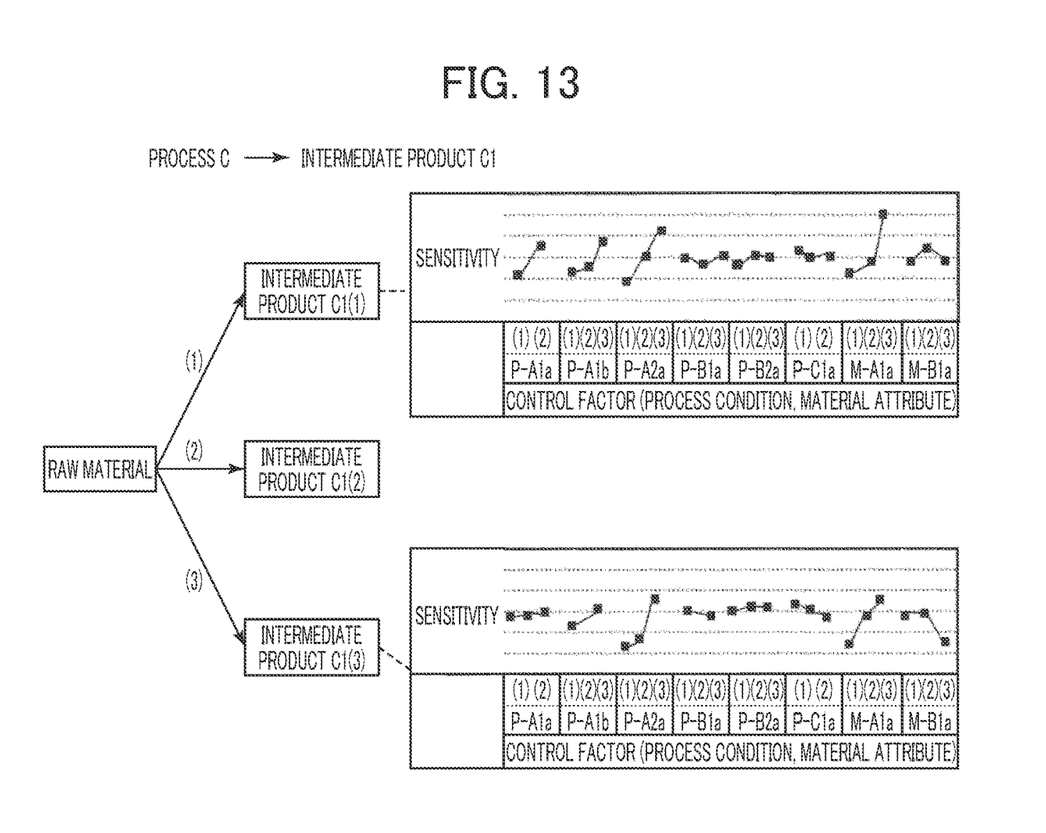
FIG. 13 is a diagram describing the influence of process conditions on functional sensitivity of each intermediate product.

FIG. 13 is a specific example of the sensitivity of each function using the factor effect diagram where the different control factors are selected. The selection of the different control factors means producing a plurality of intermediate products by changing the parameters of the control factors. Here, in the process C from the raw material, there are shown intermediate products C1a(1) and C1a(2) and an intermediate product C1(3), and their sensitivities where the set of parameters of control factors of [1], [2], and [3] (hereinafter called parameter set) is changed. When the parameter set [1] is selected from the raw material, the intermediate product C1(1) is formed, and the sensitivity at that time is linked thereto by a broken line. Further, the sensitivity of the intermediate product C1(3) where the parameter set [3] is selected from the raw material is also linked similarly.

Regarding the control factors in the process C and its upstream process, the following including the same can be seen from FIG. 13.

In the intermediate product C1(1), P-A1a, P-A1b, P-A2a, and M-A1a for the control factors are large relatively in sensitivity, and others are small relatively in sensitivity.

In the intermediate product C1(3), P-A2a, M-A1a, and M-B1a for the control factors are large relatively in sensitivity, and others are small relatively in sensitivity.

In the intermediate product C1(1) and the intermediate product C1(3), there is shown a similar tendency for sensitivity to the control factor P-A2a, but there is shown a different tendency for sensitivity to the control factor M-A1a.

Figure 11:
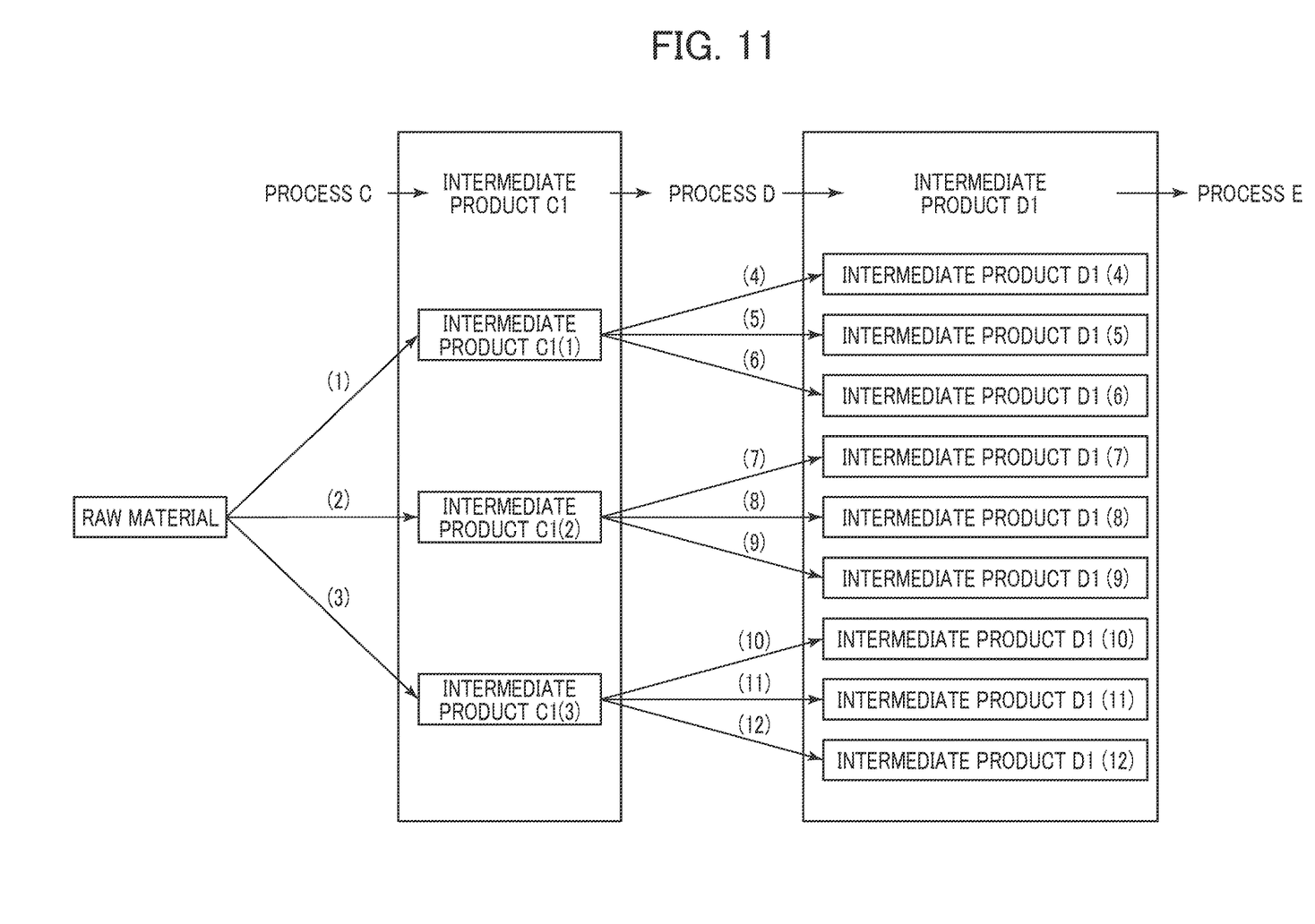
FIG. 11 is a diagram describing the branching of an intermediate product.

For example, a resin material having such manufacturing processes as shown in FIG. 11 is shown. Assume that in the manufacture of the material having such processes, a process C is a blending process, and the function of the process has viscosity. When the set of control factors in the process C is selected as [1] where the temperature is high and the reaction time is long and [3] where the temperature is low and the reaction time is short, there can be obtained an intermediate product C1(1) high in viscosity and an intermediate product C1(3) low in viscosity.

Now, assume that a process D chained from the process C is a filming process and includes the function of fluidity that the process has. When the temperature exists in parameters of control factors for each functional sensitivity related to the fluidity, the sensitivity of the temperature with respect to the fluidity becomes large in the process D of receiving the intermediate product C1(1) with the temperature set to [1]. In the process D of receiving the intermediate product C1(3) with the temperature as the parameter set to [3], the sensitivity of the temperature related to the fluidity becomes low.

In addition, the temperature also affects the functional sensitivity such as dispersibility, moldability, or the like, and the intermediate product branches more finely.

Incidentally, in the present Step, as the intermediate product, the result of actual measurement may be input. Then, information indicating the physical property of the intermediate product is identified. This is stored in the process optimization information 35 in association with the received information.

Next, in Step S206, the product management unit 21 determines until the final manufacturing process whether processing is completed up to Step S205. Specifically, it confirms whether the above Steps S203 to S205 are performed on each process indicated by the process information 31 accepted in Step S201. When each process is executed, the information is passed to Step S208.

In Step S206, when the processing is not completed until the final process, that is, when the answer is determined to be No, the product management unit 21 proceeds to Step S207. In Step S207, the product management unit 21 returns to Step S203. That is, using the material information stored in Step S206, Steps S203 to S206 are repeated until the process is determined to be the final process in Step S206. Information obtained by the repeated processing is stored in the process optimization information 35 inclusive of related information.

In Step S206, when the processing is completed up to the final process, that is, the answer is determined to be Yes, the product management unit 21 proceeds to Step S208. In Step S208, the product management unit 21 extracts a related control factor from the functional sensitivity information selected in Steps S203 to S205 and calculates a process optimization index by the central control device 11. The calculated process optimization index is stored in the process optimization information 35.

In Step S209, the product management unit 21 calculates a numeric value related to the restriction condition received in Step S202 and analyzes whether the process optimization index is converged. The product management unit 21 stores its result in the process optimization information 35 together with the series of related information. When a predetermined condition is met, the product management unit 21 specifies these information and proceeds to Step S211. When the process optimization index is not converged, the product management unit 21 proceeds to Step S210. Incidentally, the predetermined condition includes the case where the restriction condition is satisfied or the process optimization index is converged.

In Step S210, the product management unit 21 performs examination from S203 on a set of process conditions that have not been selected so far from the first process. At this time, it is also possible to use the result of the existing examination and perform examination along the process flow from any process block.

In Step S211, the display processing unit 22 outputs to the output device 13, the process optimization index specified in Step S209, the history of the process optimization index, and the process condition in each process.

Besides this, the functional sensitivity information 34 and the function/material related information 37 may be output for the arbitrary function or process condition, and the material attribute. This becomes the end of the present processing.

Incidentally, in the present embodiment, it is determined in Step S206 whether the process is the final process, and the processing after Step S203 is looping via Steps S207 and S210. However, the following alternatives may be implemented. In consideration of up to the manufacturing process in which the processing up to Step S205 has been performed, the determination of Step S209 is performed. As a result, when the restriction is met or the process optimization index is converged, the control factors in the subsequent manufacturing process are fixed as they are. In Step S209, when the restriction is not met or the process optimization index is not converged, the processing up to the next manufacturing process is executed up to S205, and the determination of Step S209 is executed.

As described above, in the processing shown in FIG. 2, the process optimization indices may be calculated collectively up to the final process. Alternatively, the process optimization indices up to each manufacturing process may be calculated stepwise. Incidentally, in the latter case, the manufacturing processes may be calculated for each plurality.

Incidentally, the meaning of each term described above is as follows.

The process condition is a condition for the manufacture in the process. An example of the process condition includes the temperature of a reactor vessel, pressure thereof, a reaction time, or the like.

The material information is material attributes associated with the type and amount (mixture ratio) of a raw material or intermediate product to be charged, the type and amount of a produced final product or intermediate product, the raw material or the intermediate product, and the final product.

The material attribute is a physicochemical property that the intermediate product or the final product has. There exist one or more of each raw material, intermediate product, and final product. An example of the material attribute includes molecular weight, molecular structure, functional group, specific gravity, melting point, boiling point, hydrogen ion concentration, the content of a specific component, or the like.

(Hierarchical Structure)

Each of the above-described process, raw material, intermediate product and function has a hierarchical structure. Regarding the process, for example, the process of a certain line includes a first process, a second process, a third process, . . . in the corresponding line. Regarding the raw material, for example, when the raw material is a mixture, a raw material A includes a plurality of mixed components A1, A2, . . . . The intermediate product is also similar. Regarding the function, for example, the oxidation rate includes an oxidation rate at each divided temperature zone. The soundproofing ability includes soundproofing ability for each divided frequency band. The malleability includes malleability in a specific direction.

Figure 3:
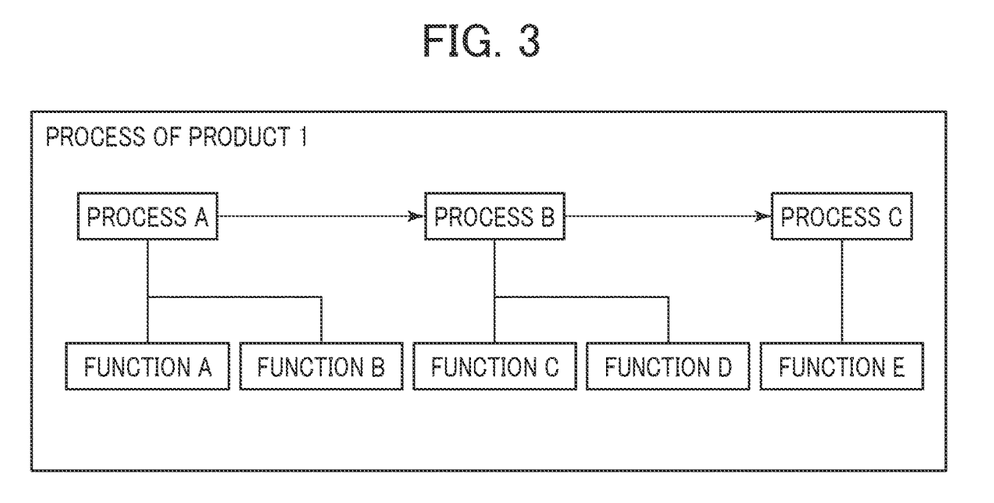
FIG. 3 is a diagram describing the relation between a process and a function.

FIG. 3 is a diagram describing the relation between process information and functional information. In the process condition 31 stored in the auxiliary storage device 15, rectangles indicating a process A, . . . , and a process C are connected by arrows in association with a product P1. The rectangles are referred to as "blocks", and the arrows are referred to as "edges". As evidenced by the orientation of the edges, these blocks are ordered in the order of the process A, the process B, and the process C. The process further encloses blocks of one or more functions. A function A, . . . , and a function E may be the same function.

As a specific example, the process A as a resin synthesis process has a functional block of viscosity and a functional block of dispersibility. Further, the process B as a heating process may have a functional block of fluidity.

(Process Information)

Figure 4:
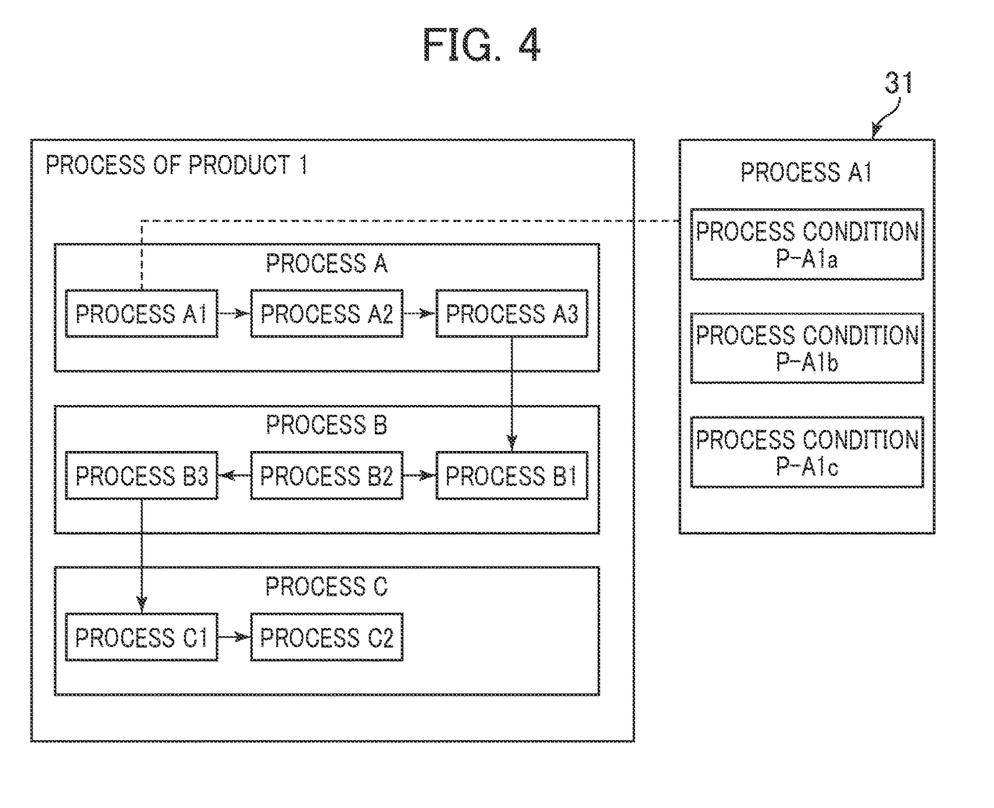
FIG. 4 is a diagram describing process information.
Figure 5:
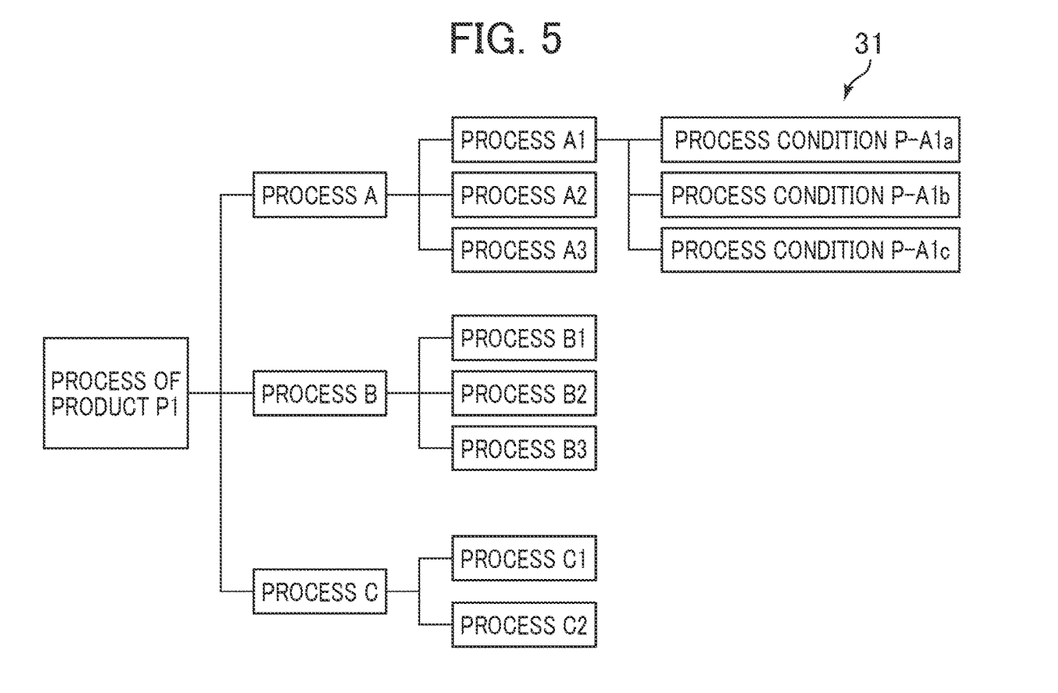
FIG. 5 is a diagram describing process information.

FIGS. 4 and 5 are diagrams describing the process information 31. First, attention is paid to FIG. 4. The process condition 31 stored in the auxiliary storage device 15 stores blocks indicating a process A1, a process A2, . . . , and a process C2 connected by arrows in association with the product P1. The process A1, the process A2, and the process A3 belong to the high-order process A. The process B1, the process B2, and the process B3 belong to the high-order process B. The process C1 and the process C2 belong to the high-order process C. The high-order processes A, B and C belong to the process of the product P1.

The process information 31 stores rectangles indicating a process condition P-A1$a$, a process condition P-A1$b$, and a process condition P-A1$c$ in association with the process A1. These rectangles are also called blocks. Although the description is omitted in FIG. 4, the process information 31 similarly stores in association with the process A2, the process A3, . . . , and the process C2, their process conditions. Eventually, by specifying "P1" as an identifier of a product, all blocks in FIG. 2, the order between the blocks, the correspondence relation between the blocks, and the hierarchical structure between the blocks are specified.

Attention is paid to FIG. 5. FIG. 5 is also the process information 31 stored in the auxiliary storage device 15. The process information 31 in FIG. 5 is substantially the same as the process information 31 in FIG. 4. The process information 31 in FIG. 5 has a "tree structure" in which the hierarchical relationship of blocks is easy to be more visible. A block indicating a "product P1" exists at the root (root, vertex) of the tree structure, and a block indicative of each process condition exists in the leaf at the end of the tree structure.

A line segment between the blocks is also called an "edge". The edge in FIG. 5 is different from the edge in FIG. 4 and does not have the orientation. However, the process information 31 may store information (e.g., a flowing raw material or intermediate product, or process condition to be taken over) between the processes in association with the edges.

There exists one piece of process information 31 for each product, and the performance of the entire process is stored for each piece of process information. The type of the process information 31 is not limited in particular, but may be the type of FIG. 4, the type of FIG. 5, or other types (e.g., a table type in which an immediately preceding process, an immediately subsequent process, a pertaining high-order process, and a process condition are stored for each process).

Here, description will be made as to a method of naming a process condition being an example of a control factor. The uppermost alphabet P indicates that it is a process condition among the control factors. Then, the alphabet and number after the hyphen indicate the process. Then, the lowercase letter of the last alphabet is applied to identify the process condition. For example, P-A1$a$ indicates a process condition $a$ of a material (or intermediate product) A1 used in a process A.

(Functional Information)

Figure 6:
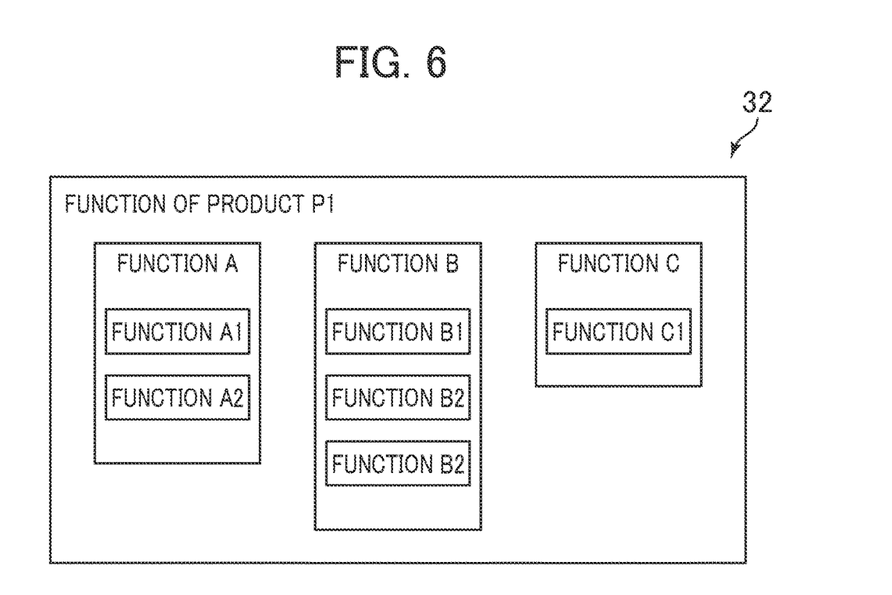
FIG. 6 is a diagram describing functional information.

FIGS. 6 and 7 are diagrams describing the functional information 32. First, attention is paid to FIG. 6. The functional information 32 stored in the auxiliary storage device 15 stored rectangles indicating a function A1, a function A2, a function B1, . . . , and a function C1 in association with a product P1. The rectangles are called "blocks". The function A1 and the function A2 belong to a high-order function A. The function B1, the function B2, and the function B3 belong to a high-order function B. The function C1 belongs to a high-order function C. The high-order functions A, B, and C belong to the product P1. By specifying "P1" as an identifier of a product, all blocks in FIG. 6 and the hierarchical structure between the blocks are specified.

Figure 7:
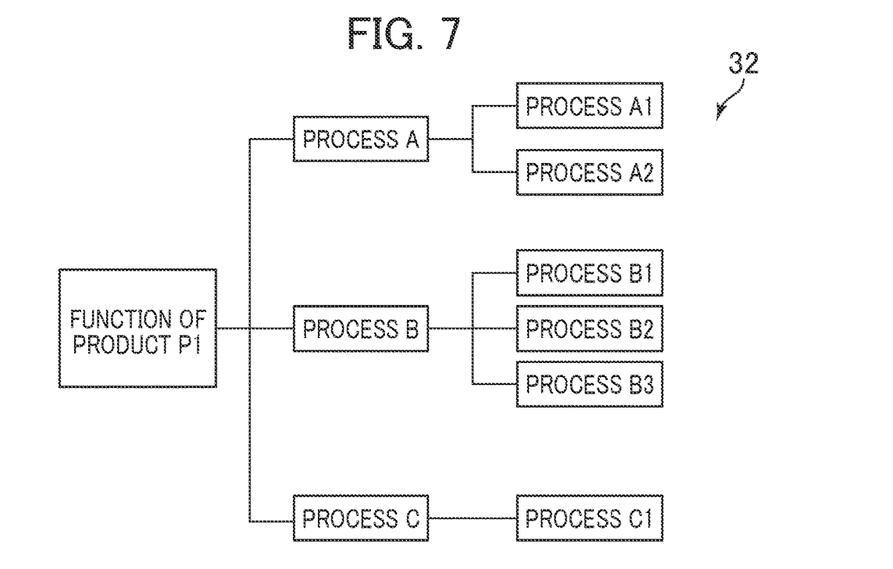
FIG. 7 is a diagram describing functional information.

Attention is paid to FIG. 7. FIG. 7 is also the functional information 32 stored in the auxiliary storage device 15. The functional information 32 in FIG. 7 is substantially the same as the functional information 32 in FIG. 6. The function information 32 in FIG. 7 has a "tree structure" in which the hierarchical relationship of blocks is easy to be more visible. A block indicating a "product P1" exists at the root of the tree structure, and a block indicative of each function exists in the leaf at the end of the tree structure. A line segment between the blocks is called an "edge". The functional information 32 may store the degree of contribution between functions or the quantitative or qualitative relationship that the function exerts, in association with the edge.

There exists one piece of functional information 32 for each product. The type of the functional information 32 is not limited in particular, but may be the type of FIG. 4, the type of FIG. 5, or other types (e.g., a table type in which pertaining high-order functions are stored for each function).

(Raw Material/Intermediate Product Information)

Figure 8:
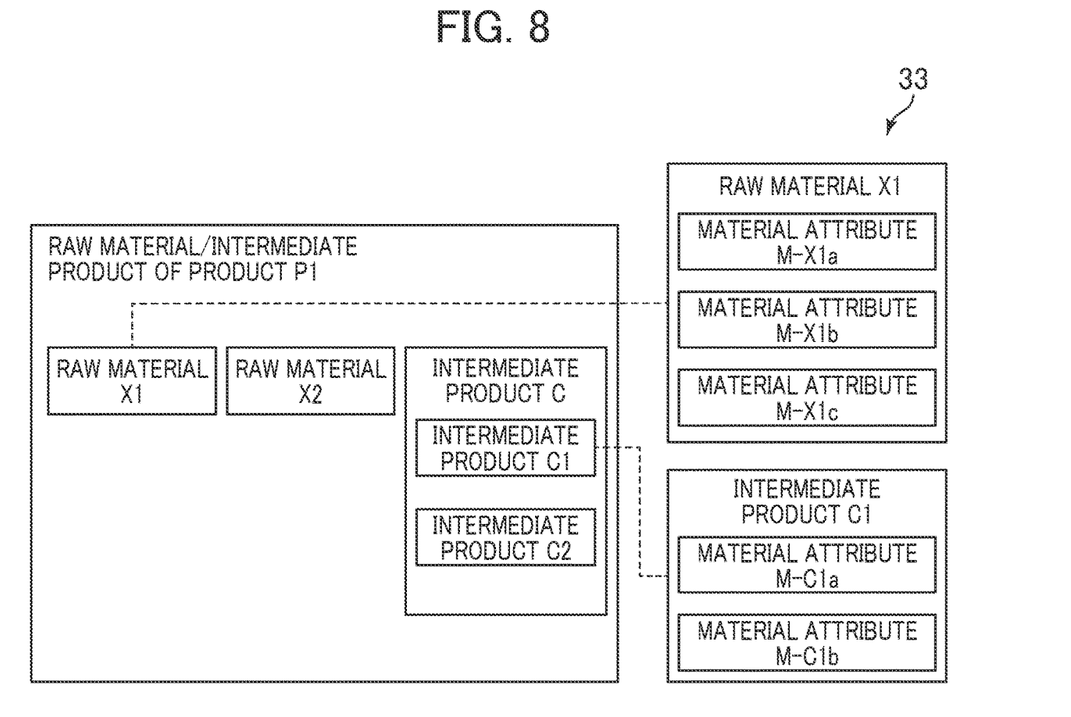
FIG. 8 is a diagram describing raw material/intermediate product information.

FIGS. 8 and 9 are diagrams describing raw material/intermediate product information 33 showing the relation between each raw material and an intermediate product and the relation between these and material characteristics. First, FIG. 8 will be described. A raw material X1, a raw material X2, and an intermediate product C belong to a raw material/intermediate product of a product P1 and are stored in the raw material/intermediate product information 33 of the auxiliary storage device 15. In the present embodiment, as described above, the processes are shown in capital letters of alphabets such as A and B, but the raw material is represented as X because no producing process is present. An intermediate product C1 and an intermediate product C2 are similarly stored in the raw material/intermediate product information 33 of the auxiliary storage device 15 in association with the product P1. Rectangles are called "blocks". The high-order intermediate products C1 and C2 belong to the high-order intermediate product C. A raw material X1 and a raw material X2 may also enclose raw materials like the intermediate product C.

The raw material/intermediate product information 33 stores rectangles indicative of a material attribute M-X1$a$, a material attribute M-X1$b$, and a material attribute M-X1$c$ in association with a raw material A1. These rectangles are also called "blocks". The raw material/intermediate product information 33 stores rectangles indicative of a material attribute M-C1$a$ and a material attribute M-C1$b$ in association with the intermediate product C1. Although the description is omitted in FIG. 8, the raw material/intermediate product information 33 similarly stores in association with the intermediate product C2, its material attributes. Eventually, by specifying "P1" as an identifier of a product, all blocks in FIG. 6, the correspondence relation between the blocks, and the hierarchical structure between the blocks are specified. Description will be made as to a method of naming the raw material and the intermediate product. The uppermost alphabet indicates a process in which the raw material and the intermediate product are produced. Further, the next number is a number for identifying a raw material or an intermediate product in the process. For example, the intermediate product C indicates intermediate products produced in the process C. When a plurality of intermediate products are produced in the process, they are identified with numbers. Incidentally, since the raw material is not managed in the manufacturing process, it is given X.

Further, a material characteristic as a control factor is named as follows. The uppermost M indicates a material characteristic among control factors. Then, the alphabet and number after the hyphen indicate the material. Further, the lowercase letter of the last alphabet is applied to identify the material characteristic. For example, M-A1$a$ indicates a material attribute a of a material (or intermediate product) A1 used in a process A.

The low-order blocks may be enclosed like the intermediate product C with respect to the raw material X1 and the raw material X2. Specifically, the raw material X includes a raw material X1, a raw material X2, a raw material X3, etc.

Figure 9:
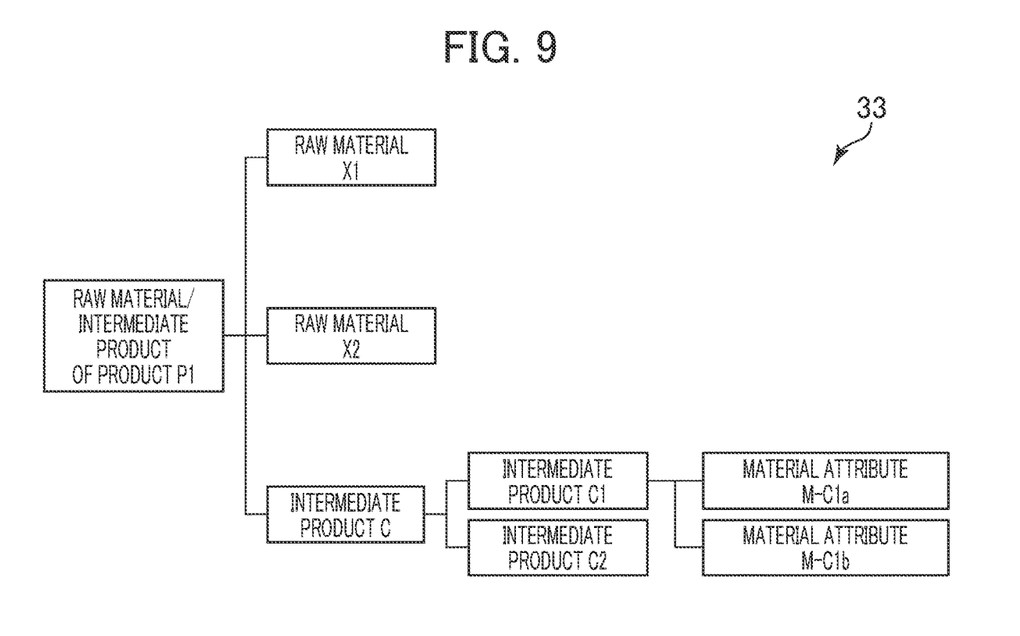
FIG. 9 is a diagram describing the raw material/intermediate product information.

Next, FIG. 9 will be described. FIG. 9 is also the raw material/intermediate product information 33 stored in the auxiliary storage device 15. The raw material/intermediate product information 33 in FIG. 9 is substantially the same as the raw material/intermediate product information 33 in FIG. 8. The raw material/intermediate product information 33 in FIG. 9 has a "tree structure" in which the hierarchical relationship of blocks is easy to be more visible. A block indicating a "product P1" exists at the root of the tree structure, and a block indicative of each material attribute exists in the leaf at the end of the tree structure. A line segment between the blocks is also called an "edge". The raw material/intermediate product information 33 may store the relation between the raw materials (e.g., conditions when the raw material is contained) in association with the edge.

There exists one piece of raw material/intermediate product information 33 for each product. The type of the raw material/intermediate product information 33 is not limited in particular, but may be the type of FIG. 8, the type of FIG. 9, or other types (e.g., a table type in which a pertaining high-order raw material (or intermediate product) and a material attribute are stored for each raw material (or intermediate product).

(Chain Diagram)

Figure 10:
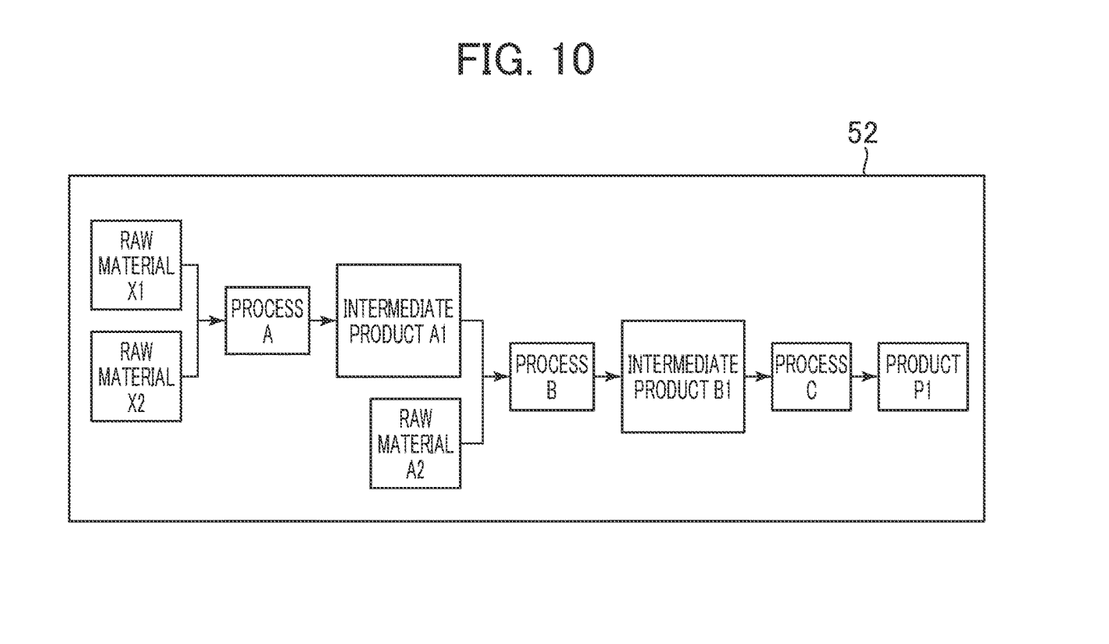
FIG. 10 is a diagram describing a chain diagram.

FIG. 10 is a diagram describing a chain diagram 52. The manufacturing process optimization system 1 is capable of creating the chain diagram 52 by using the process information 31 (refer to FIG. 4). Specifically, the manufacturing process optimization system 1 is capable of recognizing the context between the processes in the chain diagram 52 depending on the orientation of the edge in FIG. 4.

FIG. 11 is a diagram related to the branching of an intermediate product. A raw material to an intermediate product C1, . . . , an intermediate product D1, and a process E are linked by arrows. [1], . . . , and [3] written near the arrows respectively indicate a parameter set of control factors in a process C. Different intermediate products D1(4), . . . , and D1(12) are obtained from an intermediate product C1(1), . . . , and an intermediate product C1(3) produced with the parameters of the respective control factors as conditions by parameter sets [4,] . . . , and [12] of control factors in a process D. Although omitted herein, intermediate products further obtained depending on process conditions in a process E branch from the intermediate product D1.

(Function/Process Related Information)

FIG. 14 is a diagram describing the function/process related information 36 in which the control factors are process conditions. The function/process related information 36 is a matrix having process conditions in the horizontal axis (column) and functions in the vertical axis (row). There exists one piece of function/process related information 36 for each product. In the present figure, the relevance between the process condition and the function is stored in a cell at each intersection of the matrix of the function/process related information 36. A specific example of the relevance includes, for example, the following examples 1 to 4.

<Example 1> Information showing only the presence of relevance (e.g., presence=o),
<Example 2> Numerical value indicative of the degree of relevance,
<Example 3> Weight indicative of the degree of relevance (the total value for each column or row is fixed), and
<Example 4> Numerical expression indicative of the degree of relevance (function in which when the function and the process condition are indicated by numerical values, one thereof is taken as an explanatory variable and the other thereof is taken as a target function).

When no relevance exists or the relevance is unknown, information (e.g., absence=x, and unknown=?) indicating blank or unrelated or relevance-unknown may be stored.

(Function/Material Related Information)

FIG. 15 is a diagram describing the function/material related information 37 in which the control factors are material attributes. The function/material related information 37 is a matrix having material attributes in the horizontal axis (column) and functions in the vertical axis (row). There exists one piece of function/material related information 37 for each product. FIG. 15 is the function/material related information 37 for a product P1. The function/material related information 37 stores the relevance between the attribute and the function in a cell at each intersection of the matrix. A specific example of the relevance includes, for example, the following examples 5 to 8.
<Example 5> Information showing only the presence of relevance (e.g., presence=o),
<Example 6> Numerical value indicative of the degree of relevance,
<Example 7> Weight indicative of the degree of relevance (the total value for each column or row is fixed), and
<Example 8> Numerical expression indicative of the degree of relevance (function in which when the function and the material attribute are indicated by numerical values, one thereof is taken as an explanatory variable and the other thereof is taken as a target function).

When no relevance exists or the relevance is unknown, information (e.g., absence=X, and unknown=?) indicating blank or unrelated or relevance-unknown may be stored.

(Process Optimization Information)

The process optimization information 35 stores the relevance including the context between the raw material (or intermediate product) input between each process and the factor effect diagram, the selected process condition, and the calculated intermediate product (or product), the time required for manufacture and the manufacturing cost, the yield of the intermediate product or the final product, the S/N ratio, etc. A process optimization index in each process calculated from the combination of these is also stored similarly.

The process optimization index is calculated from any combination of the process optimization information 35. A specific example of the process optimization index includes a value obtained by multiplying the time (T) required for manufacture and the manufacturing cost (C), the inverse of the yield (Y), and the SN ratio (R) such as shown in the following equation 1 by arbitrary weighting factors (a, b, c, d) and adding them.

$$E=aT+bC+cY+dR \quad (1)$$

Other information may be used as an index.

In the flow chart for optimization, when the value of the process optimization index is converged to less than or equal to a numerical value to be taken as a threshold value arbitrarily set by the user, it is determined that the optimization has been performed. Besides that, the approximate curve of the process optimization index becomes flat, and the slope may be 0.

There are a method of calculating the process optimization index on all-combination all-in-one basis for the control factors and the respective functional blocks, and a method of randomly calculating the same avoiding duplication, but it is desirable to calculate the process optimization index by using machine learning.

(Usage Example)

Material information related to the functional sensitivities of some raw materials or intermediate products may not be available. Specifically, in FIG. 5, it is assumed that information on the surface tension related to the fluidity is lost in the process A2. In this case, the output device 13 outputs the following information.

Process: process A2,
Function: fluidity, and
Material information: molecular formula, surface tension.

The user is able to measure lost data, store the same in the raw material/intermediate product information 33, and temporarily input the tendency to the raw material/intermediate product information 33.

Further, it is also possible to output the function/process related information 36 related to the fluidity or the function/material related information 37 related to the fluidity, or the like. For example, when the process A2 is extremely lower than other processes in sensitivity for fluidity in the function/process related information 36, the user can also choose to ignore the data loss.

The information of the functional sensitivity may lose or be low in accuracy with respect to one product. In that case, the user is able to output the function/process related information 36 or the function/material related information 37 or both to make an experimental plan. Its result can be stored in the functional sensitivity information 34.

The user may want to know the influence of the process conditions in the process B1 in the manufacture of the product P1 having the processes shown in FIG. 10. In this case, it is possible to repeatedly verify the process B1 and the process C1 using the material information of the intermediate product C1 obtained from the process condition A1 under the condition that the set of process conditions in the process C1 is fixed.

Effects of the Present Embodiment

The effects of the manufacturing process optimization system 1 of the present embodiment are as follows.

(1) The manufacturing process optimization system 1 is capable of optimizing the manufacturing process that can obtain desired material characteristics.

(2) The manufacturing process optimization system 1 can guarantee the quality of the final product, including the management of each intermediate product.

(3) The manufacturing process optimization system 1 can guarantee the quality of the final product by stepwise quality management in the manufacturing process.

(4) The manufacturing process optimization system 1 is capable of specifying a process or a process condition, and an intermediate product that affect the function of the final product.

(5) The manufacturing process optimization system 1 can quickly respond to product defects and changes in material specification due to customer requests, etc.

(6) The manufacturing process optimization system 1 has few by-products including management of intermediate products, and can perform manufacture in consideration of the environment.

Incidentally, the present invention is not limited to the above-mentioned embodiments and includes various modifications. For example, the above-described embodiments have been described in detail in order to explain the present invention in an easy-to-understand manner, and are not necessarily limited to those having all the described configurations. Also, it is possible to replace a part of one configuration of the embodiment with the configuration of another embodiment. Further, it is also possible to add the configuration of another embodiment to the configuration of one embodiment. In addition, it is possible to apply addition/deletion/replacement of another configuration with respect to a part of the configuration of each embodiment.

Further, in regard to the above-described respective configurations, functions, processing parts and processing means, etc., some or all thereof may be realized in hardware, for example, by being designed with integrated circuits, and the like. In addition, the above-described respective configurations and functions, etc. may be realized in software by allowing a processor to interpret and execute a program realizing each function. Information about a program, a table, a file, etc. that realize each function can be put in a memory, a recording device such as a hard disk, an SSD (Solid State Drive) or the like, or a recording medium such as an IC card, an SD card, a DVD or the like.

In addition, control lines and information lines indicate what is considered necessary for explanation, but do not necessarily indicate all controls lines and information lines on the product. In practice, it may be considered that almost all configurations are interconnected.

LIST OF REFERENCE SIGNS

1 . . . manufacturing process optimization system,
11 . . . central control device,
12 . . . input device,
13 . . . output device,
14 . . . main storage device,
15 . . . auxiliary storage device,
21 . . . product management unit,
22 . . . display processing unit,
31 . . . process information,
32 . . . functional information,
33 . . . raw material/intermediate product information,
34 . . . functional sensitivity information,
35 . . . process optimization information.

The invention claimed is:

1. An optimization system of a manufacturing process comprised of a plurality of processes, comprising:
a processor;
a display coupled to the processor; and
a memory, coupled to the processor, storing instructions that when executed by the processor, configure the processor to:
receive factor information including a plurality of control factors of each of the processes, and restriction information serving as a restraint in the manufacturing process, each control factor including a a material attribute or a process condition,
calculate a functional sensitivity indicating a degree of influence to the manufacturing process for each control factor and for each of a plurality of products produced in the manufacturing process,
display, on the display, respective factor effect diagrams for each of the respective products produced in the manufacturing process, each diagram showing, at least one process condition, as a first control factor, in combination with a plurality of first parameters of the process condition, and at least one material attribute as a second control factor, in combination with a plurality of second parameters of the material attribute on a first axis and, on a second axis, the calculated functional sensitivity for each combination of each first control factor and the plurality of first parameters and each combination of each second control factor and the plurality of second parameters,
select one of the first control factor and the second control factor based on respective calculated functional sensitivities,
specify a physical property of an intermediate product in each process by using the selected control factor,
determine using the specified physical property of each intermediate product whether the control factor satisfies a predetermined condition, and
display, on the display, the control factor having satisfied the predetermined condition.

2. The optimization system of the manufacturing process according to claim 1,
wherein the processor is configured to:
select the control factor by using the combinations of the material attributes and the process conditions and the function of the intermediate product.

3. The optimization system of the manufacturing process according to claim 2,
wherein the combinations of the material attributes and the process conditions includes information indicating the presence or absence of the relevance of the control factor to the function of the intermediate product, and
wherein the processor is configured to select the control factor indicating the presence of the relevance.

4. The optimization system of the manufacturing process according to claim 2,
wherein the combinations of the material attributes and the process conditions includes information indicating the degree of the relevance of the control factor to the function of the intermediate product, and
wherein the processor is configured to select the control factor whose relevance is more than a predetermined value.

5. An optimization method of a manufacturing process using an optimization system of a manufacturing process comprised of a plurality of processes, comprising the steps of:
receiving factor information including a plurality of control factors of each of the processes, each control factor including a material attribute or a process condition;
receiving restriction information serving as a restraint in the manufacturing process;
calculating a functional sensitivity indicating a degree of influence to the manufacturing process for each control factor and for each of a plurality of products produced in the manufacturing process;
displaying, on a display, respective factor effect diagrams for each of the respective products produced in the manufacturing process, each diagram showing, at least one process condition, as a first control factor, in combination with a plurality of first parameters of the process condition, and at least one material attribute as a second control factor, in combination with a plurality of second parameters of the material attribute on a first axis and, on a second axis, the calculated functional sensitivity for each combination f each first control factor and the plurality of first parameters and each combination of each second control factor and the plurality of second parameters;

selecting one of the first control factor and the second control factor based on respective calculated functional sensitivities;

specifying a physical property of an intermediate product in each process by using the selected control factor;

determining using the specified physical property of each intermediate product whether the control factor meets a predetermined condition; and displaying, on the display, the control factor having satisfied the predetermined condition.

6. The optimization method of the manufacturing process according to claim 5, further comprising the step of:

selecting the control factor by using function/factor related information indicating the relevance of the control factor and the function of the intermediate product.

7. The optimization method of the manufacturing process according to claim 6, wherein the combinations of the material attributes and the process conditions indicate a presence or absence of a relevance of the control factor to the function of the intermediate product, and wherein the method further comprises, upon selecting the control factor, selecting the control factor indicating the presence of the relevance.

8. The optimization method of the manufacturing process according to claim 6, wherein the combinations of the material attributes and the process conditions indicate a degree of a relevance of the control factor to the function of the intermediate product, and wherein the method further comprises, upon selecting the control factor, selecting the control factor whose relevance is more than predetermined.

* * * * *